United States Patent [19]

Kee

[11] Patent Number: 5,664,594
[45] Date of Patent: Sep. 9, 1997

[54] CLEANING DEVICE FOR VENTILATOR MANIFOLD AND METHOD OF USE THEREOF

[75] Inventor: Kok-Hiong Kee, St. Louis, Mo.

[73] Assignee: Sherwood Medical Company, St. Louis, Mo.

[21] Appl. No.: 366,152

[22] Filed: Dec. 29, 1994

[51] Int. Cl.[6] .................................................. B08B 9/03
[52] U.S. Cl. .................. 134/22.11; 134/24; 134/166 R; 134/198; 134/182; 134/183; 15/302
[58] Field of Search .................. 15/320, 302; 239/104; 134/182, 183, 198, 166 R, 22.1, 24, 22.11, 22.12; 141/312, 389, 388, 370; 222/570

[56] References Cited

U.S. PATENT DOCUMENTS

| 457,603 | 8/1891 | Fox | 134/182 |
|---|---|---|---|
| 1,988,198 | 1/1935 | German | 134/167 C |
| 2,005,385 | 6/1935 | O'Hara | 134/167 R |
| 2,016,148 | 10/1935 | Vartanian | 134/167 R |
| 2,490,422 | 12/1949 | Denison | 134/167 C |
| 2,896,643 | 7/1959 | Ottoson | 15/302 |
| 3,120,237 | 2/1964 | Lang | 134/167 R |
| 3,352,333 | 11/1967 | Glasgow et al. | 141/312 |
| 3,770,204 | 11/1973 | Schuster | 134/183 X |
| 3,849,830 | 11/1974 | Wagner | 15/302 |
| 3,916,924 | 11/1975 | McGowan | 134/168 R |
| 4,053,284 | 10/1977 | Posch | 15/302 |
| 4,106,155 | 8/1978 | Fosslien | 15/321 |
| 4,182,591 | 1/1980 | Stanelle | 141/388 |
| 4,580,556 | 4/1986 | Kondur | 128/206.28 |
| 4,702,267 | 10/1987 | Ashraff | 134/198 |
| 5,060,646 | 10/1991 | Page | 128/207.14 |
| 5,078,131 | 1/1992 | Foley | 128/203.15 |
| 5,125,893 | 6/1992 | Dryden | 604/54 |
| 5,255,676 | 10/1993 | Russo | 128/207.14 |

FOREIGN PATENT DOCUMENTS

| 806337 | 12/1936 | France | 134/167 R |
|---|---|---|---|
| 596429 | 6/1932 | Germany | 141/389 |
| 3734846 | 10/1987 | Germany . | |
| 961805 | 9/1982 | U.S.S.R. | 134/167 R |
| WO94/05592 | 3/1994 | WIPO | 141/312 |

*Primary Examiner*—Frankie L. Stinson
*Attorney, Agent, or Firm*—Ari M. Bai

[57] ABSTRACT

A method and apparatus for the cleaning of a ventilator manifold while it is attached to a respiratory support system. A particular embodiment of the present invention relates to a cleaning device used in conjunction with the ventilator manifold to clean the interior chamber of the manifold of patient secretions that have accumulated during the use of the manifold. The cleaning device includes a dual lumen catheter which accesses one of a plurality of manifold ports by inserting the cleaning device through a flexible boot attached to one of the manifold ports. The flexible boot allows for omni-directional use of the cleaning device inside the manifold by medical personnel. The use of the flexible boot in combination with the cleaning device allows medical personnel to cleanse the interior of the manifold without concurrent loss of respiratory support to the patient.

11 Claims, 4 Drawing Sheets

CLEANING DEVICE FOR VENTILATOR MANIFOLD AND METHOD OF USE THEREOF

BACKGROUND OF THE INVENTION

1. Field of the Invention

This invention relates generally to a manifold cleaning device. More specifically, the present invention relates to a method and apparatus for the cleaning of a ventilator manifold while it is attached to a respiratory support system. Even more specifically, the present invention relates to a cleaning device used in conjunction with the ventilator manifold to clean the interior central chamber of the ventilator manifold of patient secretions that have accumulated during use of the manifold.

2. Prior Art

Respiratory support systems used for the ventilation of critically ill patients are now commonly used in medical facilities. Typically, a prior art respiratory support system includes a tracheal tube, positioned either directly or through the nose or mouth into the trachea of a patient, and a ventilator manifold connected to the tracheal tube and to a source of breathable gas. The ventilator manifold also contains a third port, called the "weaning" port, for weaning patient's off the respiratory support system using direct atmospheric air as an oxygen source for the patient, and a fourth port used for attaching accessory devices, such as a sheathed suction catheter, to the manifold. When a patient is attached to the respiratory support system, the suction catheter attached to the accessory access port is periodically used to aspirate the patient's lungs, however contaminants from the patient's secretion tend to coat both the catheter tube as well as the interior chamber of the manifold during use. As a result, the catheter must be cleaned after each use.

U.S. Pat. No. 3,991,762 to Radford is exemplary of the general prior art effort to solve this cleaning problem. The Radford device includes a small cleaning opening in its manifold accessory access port which allows cleaning liquid to be sprayed onto the tip of the withdrawn catheter, which is then suctioned into the catheter. The result is a rinsing of the secretions from the distal end of the catheter.

Nevertheless, Radford fails to address the problem of secretion accumulation in the interior chamber of the ventilator manifold. Instead of being cleaned by this process, Radford's interior chamber becomes increasingly coated with secretions that prevent necessary observation of the mucus by medical personnel. Further, this accumulation of secretions makes viewing of the ventilator manifold aesthetically distracting. The ventilator manifold must allow for clear viewing of its interior chamber so that the mucus from the patient's lungs may be examined by medical personnel as it is being expectorated by the patient in order to assist them in accessing the patient's condition. When the interior chamber becomes clogged with secretions over time, viewing the condition of mucus being expectorated by the patient becomes exceedingly difficult. Existing prior art procedures require disconnecting the patient from the respirator by first disconnecting the manifold from the patient's tracheal tube and leaving the patient off the ventilation system while the medical assistant cleans the inside of the manifold with a saline solution and then shakes the manifold dry of any remaining residue. However, interruption of the patient's ventilation in this manner is generally contra-indicated due to the stress on the patient's respiratory system while off the respirator.

As of yet, nothing in the prior art has addressed the problem of properly and effectively cleansing the interior chamber of the manifold in order to extend the useful life thereof without a concurrent loss of ventilator assisted respiratory support to the patient. Specifically, there has been no design consideration for the attachment of a cleaning device to the manifold body that will effectively cleanse and evacuate secretions and other contaminants from the interior chamber of the manifold. Moreover, no procedural consideration has existed for properly cleaning the inside of the ventilator manifold without concurrent loss of respiratory support to the patient.

There therefore exists a need in the art for a ventilator manifold which is designed to allow direct access to its interior chamber for cleansing it of unsightly contaminants which accumulate during use.

BRIEF SUMMARY AND OBJECT OF THE INVENTION

In brief summary, the present invention overcomes and substantially alleviates the deficiencies in the prior art by providing a cleaning device and method thereof for accessing and cleansing secretions from the interior chamber of a ventilator manifold.

Accordingly, it is the principle object of the present invention to provide a reliable, medical, cleaning device usable in combination with a ventilator manifold for cleaning the manifold of secretions.

Another object of the present invention is to provide a ventilator manifold which includes a weaning port and an accessory port that allows a cleaning device direct access to the interior chamber of the ventilator manifold using either port.

A further object of the present invention is to provide a cleaning device which maintains a sealed environment around the ventilator manifold when positioned therein for cleaning.

These and other objects of the present invention are realized in a presently preferred embodiment thereof, described by way of example and not necessarily by way of limitation, which provides for the attachment of a cleaning device, having a flexible boot, to the "weaning" port or accessory port of a ventilator manifold thereby allowing medical personnel to directly clean the interior chamber of the ventilator manifold with the cleaning device.

DETAILED DESCRIPTION OF THE PREFERRED EMBODIMENTS

As shown in the exemplary drawings for the purposes of illustration, an embodiment of a ventilator manifold made in accordance with the principles of the present invention, referred to generally by reference 10, is provided in conjunction with a cleaning device, referred to generally by reference 11, for facilitating the cleansing of the interior chamber of the manifold 10 by utilizing one of the standard ports found on the manifold 10 for direct access therein.

Figure 1:
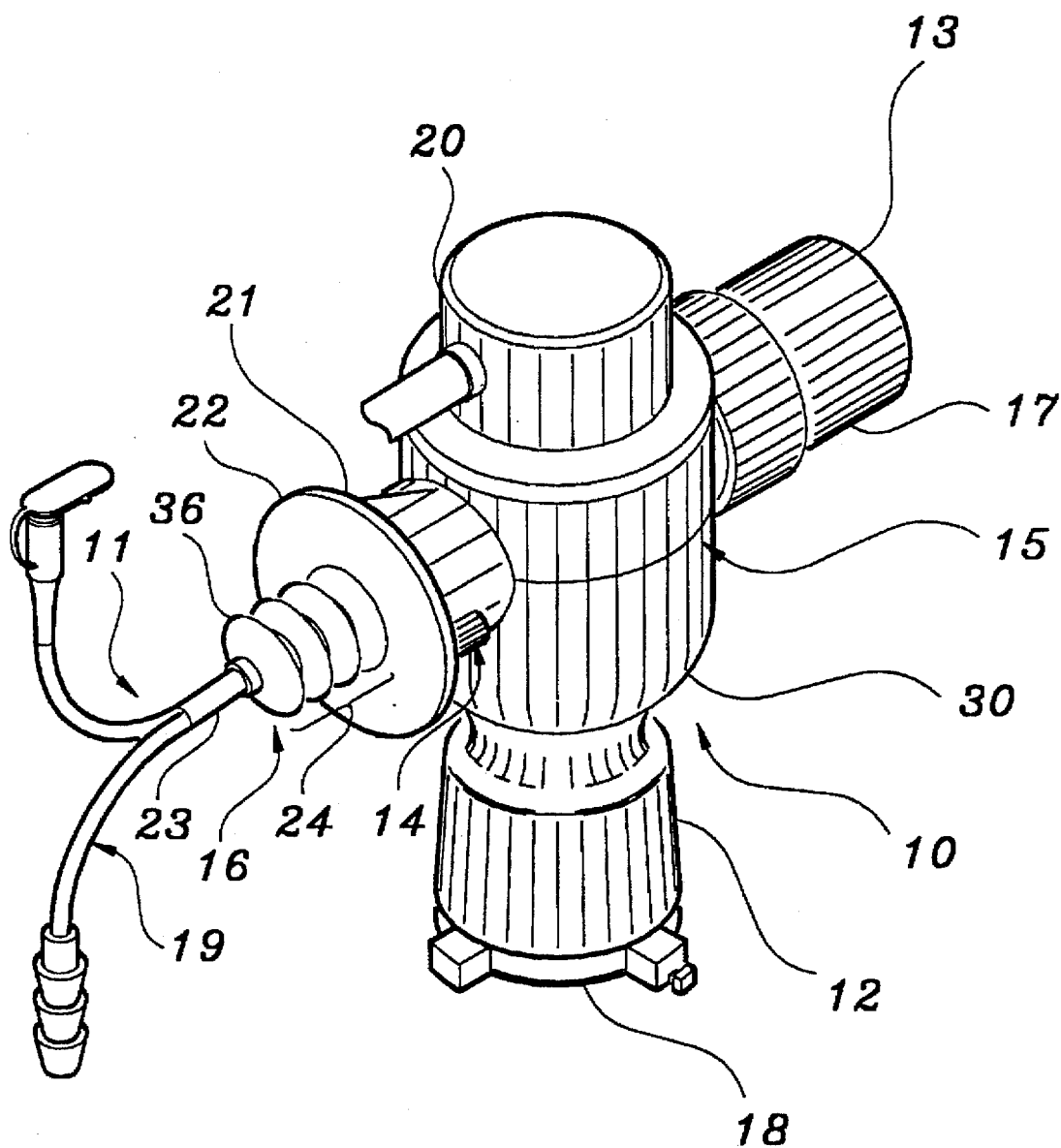
FIG. 1 is a perspective view of the ventilator manifold and cleaning device of the present invention.

As shown in FIG. 1, the preferred embodiment of the ventilator manifold 10 in conjunction with a cleaning device 11 of the present invention includes a plurality of ports which facilitate its connection to a patient and to a ventilator circuit of the respiratory support system. The ventilator manifold 10 is attached to the patient for fluid flow communication with the patient's lungs by the connection of the tracheal attachment port 12 thereof to the connector of an endotracheal assembly (not shown) which has been previously positioned in the trachea of a patient by any one of several well known procedures.

The accessory attachment port 20, located opposite of the tracheal attachment port 12, serves to attach and detach accessory devices thereto without interruption of continuous respiratory support to the patient. Many important aspects of the accessory port 20 of the present invention are disclosed in applicant's U.S. Pat. No. 5,333,607 by Kee et al, which is incorporated herein by reference in its entirety.

A ventilator circuit port 13 of the ventilator manifold 10 is connected to flexible breathing hoses from the respiratory support system (not shown) in a well known manner, such as through a "Y" site connector.

The ventilator circuit connection port 13 and the patient attachment port 12 may, if desired, include swivel connectors 17 and 18 respectively thereon in order to allow relative rotation between the ventilator manifold 10 and the trachea tube from the incidental forces caused by the manifold 10 or the breathing hoses attached thereto so as to increase the comfort of the patient.

The ventilator circuit attached to port 13 provides a high oxygen content gas mixture to the patient and receives the expelled air from the patient. The ventilator circuit commonly includes various valves, regulators and the like associated with the hoses attached to the port 13 to effect respiration of the patient. The ventilator manifold 10, and hoses attached thereto at the ventilator circuit port 13 are intended to be used by only one patient and then discarded.

The interior chamber 15 is made of a transparent material that allows medical personnel to view the inside of the chamber 15. The lower section of the interior chamber 15 includes a lip portion 30 that extends upward from the patient attachment port 12 and forms a lip that serves to collect secretions coughed up by the patient into the chamber 15.

When attached to the patient, the entire respiratory system is designed to isolate the patient's lungs from the atmosphere and allow pressurized forced ventilation of a gas mixture of a high oxygen content from the ventilator into the patient's lungs. Commonly, respiratory support systems of this type are used to maintain a positive end expiratory pressure (PEEP) within the ventilator manifold 10 and the patient's lungs at all times during exhalation. This technique is used because of its benefit of ensuring that a minimum concentration of oxygen is supplied to the patient to maintain proper blood oxygenation levels. The PEEP procedure keeps a large number of lung alveoli of the patient open at all times during respiratory support, thus increasing the effective lung area subject to ventilation.

Prevailing respiratory support techniques, including PEEP, have made it disadvantageous to interrupt respiratory support to the patient in order to either clean the catheter being used to aspirate the patient's lungs or cleanse the interior chamber 15 of the ventilator manifold 10 so that medical personnel may view the color and condition of mucus being expectorated by the patient inside the interior chamber 15.

Catheters, under normal medical practice, must be disposed of after each use or they must be cleaned, such as in the manner described in the above mentioned Radford patent, by injecting cleaning fluid into the access port of the manifold in order to wash the withdrawn catheter tip. As yet however, no apparatus or method has been developed to clean the interior chamber 15 of the manifold 10 without disconnecting the manifold 10 from the respiratory support system so that medical personnel could inject a saline solution into the chamber 15 and then shake dry the manifold 10 before reattaching it to the respiratory support system. When this procedure takes an extended period of time to perform, the patient's blood oxygen levels can drop to inadequate levels, and cause the patient to over exert the lungs and heart when trying to return the blood oxygenation level to normal. Also, disconnecting the ventilator manifold 10 in order to cleanse the interior chamber 15 may expose the manifold 10 to contaminants.

The present invention resolves the problems associated with loss of isolation of the respiratory support system from the atmosphere (i.e. loss of PEEP) when medical personnel must cleanse the interior chamber 15. Specifically, the ventilator manifold 10 of the present invention includes the attachment of a cleaning device 11 so as to allow direct access to the interior chamber 15 by the cleaning device 11 in order to cleanse the chamber 15 of secretions, or to clean a withdrawn or partially withdrawn catheter which was previously used to aspirate a patient's lungs within the confines of the chamber 15, without loss of PEEP.

Figure 2:
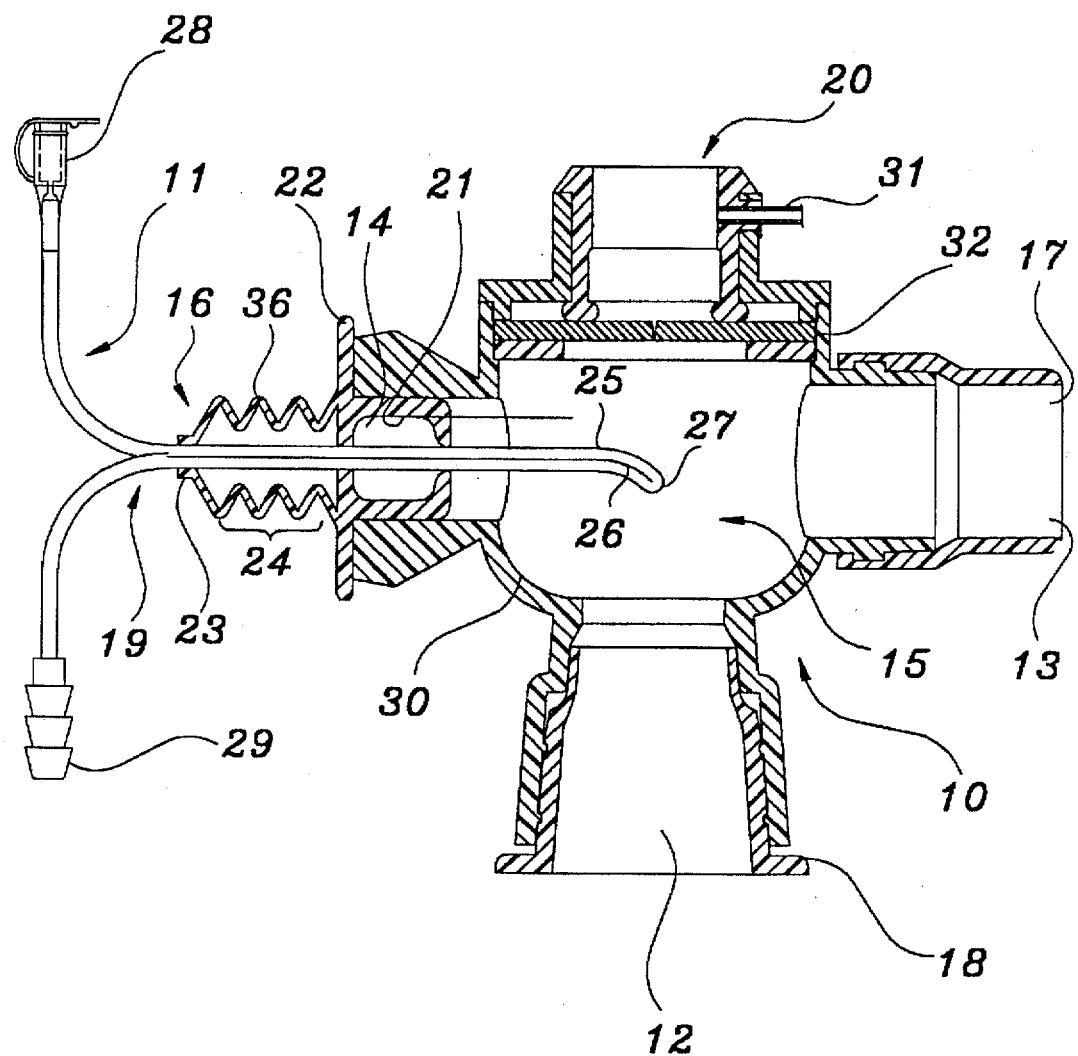
FIG. 2 is a cross-sectional view of the ventilator manifold and cleaning device of the present invention.
Figure 3:
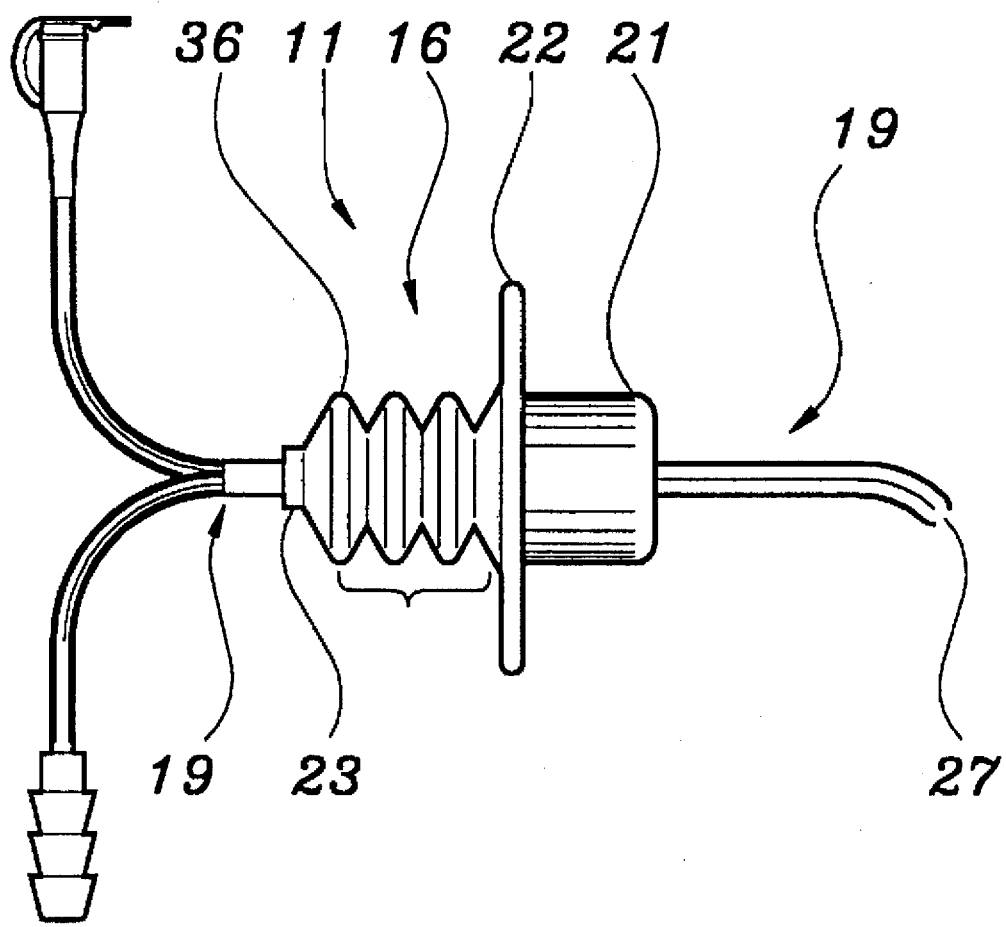
FIG. 3 is a perspective of the cleaning device of the present invention.

As best shown in FIG. 3, the cleaning device 11 includes a flexible boot 16 in conjunction with a cleaning tube 19, or the like. In the preferred embodiment, the cleaning tube 19 is inserted through the weaning port 14 (see FIG. 2), but may also be inserted through the accessory access port 20 (see FIG. 2) if desired. The flexible boot 16 can be made of any flexible polymer or plastic elastomer.

The distal end of the flexible boot 16 preferably comprises an insertion member 21 which forms a tight fit on the inside of the weaning port 14, and a flange 22 formed at the proximal end of the insertion member 21 opening of weaning port 14. The proximal end of the boot 16 includes an attachment portion 23 for holding the cleaning tube 19 in position for insertion into the interior chamber 15 (see FIG. 2). Interposed between the attachment portion 23 and the flange 22 is an accordion portion 24 which allows omnidirectional adjustment of the cleaning tube 19 within the interior chamber 15.

In the preferred embodiment shown in FIG. 2, the cleaning tube 19 of the cleaning device 11 includes an upper lumen 25 and a lower lumen 26 which both terminate in a common distal opening 27. The proximal end of the upper lumen 25 includes a connector 28 which may be connected to an irrigation source (not shown) for injecting a saline solution, or the like, into the interior chamber 15 in order to wash off secretions that build up on the surface of the chamber 15. The proximal end of the lower lumen 26 includes a barbed connector 29 for connection to an aspiration source (also not shown) for evacuating secretions from the interior chamber 15.

The cleansing operation may involve only irrigating or aspirating the interior chamber 15 of the ventilator manifold 10 rather than a simultaneous irrigation and aspiration operation. If an irrigation-only operation is conducted to cleanse the manifold 10 than medical personnel can "gravity dry" the manifold 10 by disconnecting the flexible boot 16 from the weaning port 14 and swiveling the manifold 10 in order to allow the irrigated fluids to flow out of the port 14 until the manifold is sufficiently dry.

The preferred method of operating the cleaning device 11 first involves attaching the cleaning tube 19 to the flexible boot 16. After uncapping the weaning port 14, or alternatively the accessory access port 20, the cleaning tube 19 and boot 16 combination is then inserted into the port 14 by inserting the insertion member 21 of the boot 16 into the port 14 until the port 14 abuts the flange 22 thereby securing the boot 16 to the port 14 and forming an air tight seal thereto.

It is preferred that the cleaning tube 19 be formed separately and then attached to the boot 16 prior to the boot 16 being attached to the weaning port 14. The attachment of the cleaning tube 19 to the boot 16 may be accomplished by either stretch fitting the boot 16 onto the cleaning tube 19 at its midpoint or by applying an adhesive bond to the boot opening 23 in order to form an air tight seal with the cleaning tube 19 at the same midpoint.

In an alternative embodiment, the cleaning tube 19 can be integrally formed to the attachment portion 23 of the boot 16 so as to be inserted into the interior chamber 15 at the time of attaching the boot 16 to the weaning port 14.

Once the cleaning tube 19 is inserted into the interior chamber 15, medical personnel may maneuver the cleaning tube 19 in an omni-directional manner in order to clean the surface of the chamber 15 of secretions. It is intended that the boot 16 facilitate the translational movement of the cleaning tube 19 within the interior chamber 15 by use of the accordion portion 24. The accordion portion 24 forms a bellows shape that comprises a series of expansible pleats 31 made of a elastomeric material that allows the portion 24 to effect the translational movement of the cleaning tube 19 within the interior chamber 15 when medical personnel are cleansing the inside of the ventilator manifold 10. The expansible pleats 31 are flexible enough that the cleaning tube 19 can also be manipulated in a rotational manner, which along with the translational movement, affords a completely omni-directional positionability to the cleaning device 11 sufficient to access all interior surface areas of the interior chamber 15.

Once the cleaning operation has sufficiently cleansed the interior chamber of secretions, the cleaning tube 19 is withdrawn from the interior chamber 15 by either removing the entire cleaning tube 19/boot 16 combination from the weaning port or withdrawing the boot 16 after first removing the cleaning tube 19. Finally, the weaning port 14 is recapped. In this manner, the interior chamber 15 of the ventilator manifold 10 is clean of secretions without significant interruption of continuous respiratory support of the patient by the respiratory support system and with no noticeable loss of isolation of the respiratory support system from the atmosphere.

Alternatively, the cleansing operation may be performed by inserting the cleaning device 11 in the manifold 10 through the accessory access port 20 instead of through the weaning port 14. Insertion of the cleaning device 11 into the accessory access port 20 is accomplished in a similar manner as explained above with respect to the weaning port 14, however insertion of the flexible boot 16 into the accessory access port 20 causes the insertion member 21 of the boot 16 to close off the pigtail opening 31. When the flange 21 of the boot 16 abuts the side members 33 of the accessory access port 20, the boot 16 is fully engaged. Cleaning tube 19 is then inserted through the boot 16 and the closure valve 32 until the tube 19 enters the interior chamber 15. The cleansing operation is then conducted in the same manner as described above.

Figure 4:
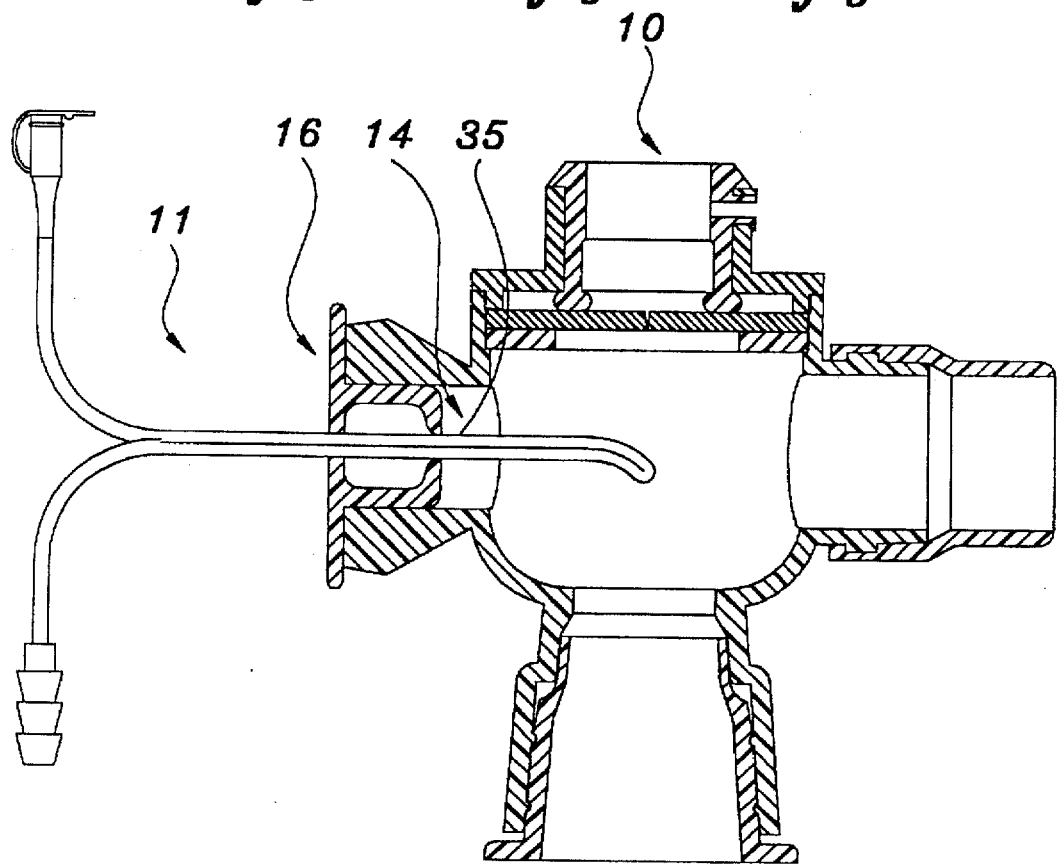
FIG. 4 is a cross-sectional view of the ventilator manifold and cleaning device showing the alternate embodiment of the boot.

In an alternative embodiment shown in FIG. 4, the flexible boot 16 is shaped as a plug and is used to cap the weaning port 14 while also functioning as part of the cleaning device 11. The boot 16 is attached to the weaning port 14 in the same manner as mentioned above by inserting the boot 16 into the port 14 opening until the flange 22 abuts the port 14 and securely engages the boot 16 to the weaning port 14.

Figures 5, 6, 7, 8:
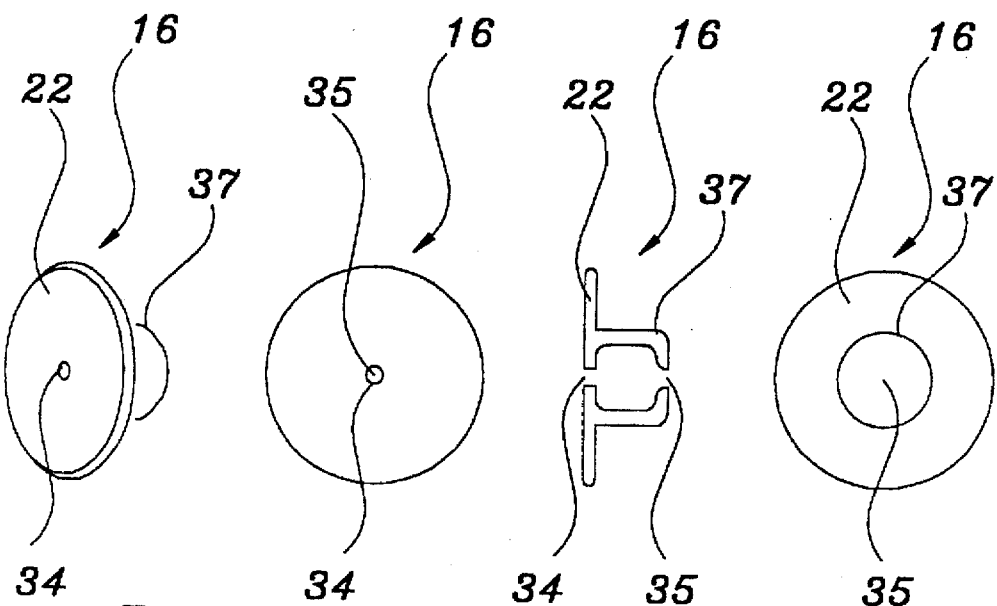
FIG. 5 is a perspective of the boot of the alternate embodiment.
FIG. 6 is a top view of FIG. 5 of the alternate embodiment.
FIG. 7 is a cross-sectional side view of the alternate embodiment.
FIG. 8 is a bottom view of FIG. 5 showing the alternative embodiment.

Referring now to FIG. 5, the alternate embodiment of boot 16 shall now be described in greater detail. The boot 16 includes an annular-shaped flange 22 integrally attached to a sealing member 37 with the boot 16 having an opening 34 with approximately the same diameter as the cleaning tube 19 in order to allow for easy access of tube 19. FIG. 6 is a bottom view of the boot 16 showing the slit 35 at the distal end of opening 34. The slit 35 is preferably composed of an elastomeric material which forms an air tight seal, but is flexible enough to allow entry of the tube 19 therethrough when the tube 19 is pressed against the slit 35.

FIG. 7 is a cross-section of the boot 16 showing the relationship of opening 34 to slit 35 of boot 16 while FIG. 8 shows a top view of same boot 16 with slit 35 shown at its distal end. The advantage of the alternate embodiment is that no connecting and disconnecting of the boot 16 from the manifold 10 is required, therefore the air tight integrity of the respiratory support system is maintained while the cleansing operation is being conducted. Moreover, the boot 16 of the alternative embodiment requires no prior attachment of the cleaning tube 19 to the boot 16 before insertion of the boot 16 onto the weaning port 14.

Although particular embodiments of the invention have been shown, it is not intended that the invention be limited thereby, instead, the scope of the present invention is intended to be limited only by the appended claims.

I claim:

1. A cleaning device for cleaning an interior chamber of a manifold having at least one port therein, said cleaning device comprising:

a) a flexible boot attachable to the at least one port of the manifold for sealing said flexible boot to the at least one port;

b) a cleaning tube attachable to said flexible boot, whereby attachment of said flexible boot to both the at least one port and said cleaning tube positions said cleaning tube at least partially within the interior chamber of the manifold and allows for omni-directional adjustment of said cleaning tube within the manifold, wherein said cleaning tube is a dual lumen catheter having a first lumen and a second lumen, said first lumen including a distal end and proximal end wherein said proximal end of sad first lumen includes a connector for connection to an irrigation means, and said second lumen includes a distal end and proximal end wherein said proximal end of said second lumen includes a connector for connection to an aspiration means, whereby said first lumen and said second lumen can irrigate and aspirate said interior chamber simultaneously, said catheter being attached to said flexible boot.

2. The cleaning device according to claim 1, wherein the flexible boot includes expansible pleats.

3. The cleaning device according to claim 2, wherein said expansible pleats further allow translational movement of said cleaning tube relative to the manifold.

4. The cleaning device according to claim 3, wherein said expansible pleats form an accordion-like shape.

5. The cleaning device according to claim 1, wherein said flexible boot is integrally formed with said cleaning tube.

6. The cleaning device according to claim 1, wherein said cleaning tube further includes a flexible tip at its distal end.

7. A method of cleaning a manifold having an interior chamber and at least one port with a cleaning device, including a cleaning tube having distal and proximal ends, and flexible boot, wherein the manifold is a ventilator manifold connected to a respiratory support system, said ventilator manifold having a weaning port, said method comprising the steps of:

a) attaching the flexible boot to the at least one port, said step of attaching further including attachment of the flexible boot to said weaning port;

b) inserting the distal end of the cleaning tube through the flexible boot and into the interior chamber of the manifold;

c) connecting the proximal end of the cleaning tube to a source of aspiration;

d) aspirating the interior chamber with the cleaning tube;

e) disconnecting the flexible boot from the at least one port.

8. The method of cleaning a ventilator manifold according to claim 7, wherein the manifold is a ventilator manifold connected to a respiratory support system, said ventilator manifold having an accessory attachment port, said step of attaching further comprises attachment of the flexible boot to said accessory attachment port.

9. A method for cleaning the interior chamber of a manifold having an interior chamber and at least one port with a cleaning device having distal and proximal ends, the cleaning device including a cleaning tube and flexible boot, said method comprising the steps of:

a) attaching the flexible boot to the at least one port;

b) inserting the distal end of the cleaning tube through the flexible boot and into the interior chamber of the manifold, wherein said step of inserting further includes inserting a cleaning tube having dual lumens, said dual lumens further comprising a first lumen and a second lumen, wherein said first lumen includes a distal end and a proximal end, said proximal end of said first lumen including a connector for connection to an aspiration means, and wherein said second lumen including a distal end and a proximal end, said proximal end of said second lumen includes a connector for connection to an irrigation means, whereby said first lumen and said second lumen can irrigate and aspirate the interior chamber simultaneously.

10. The method of cleaning the manifold according to claim 9, wherein the manifold is a ventilator manifold connected to a respiratory support system, said ventilator manifold having a weaning port, said step of attaching further comprises attachment of the flexible boot to said weaning port.

11. The method of cleaning the ventilator manifold according to claim 9, wherein the manifold is a ventilator manifold connected to a respiratory support system, said ventilator manifold having an accessory attachment port, said step of attaching further comprises attachment of the flexible boot to said accessory attachment port.

* * * * *